United States Patent
Takahashi et al.

(10) Patent No.: US 11,145,094 B2
(45) Date of Patent: Oct. 12, 2021

(54) IMAGE RECONSTRUCTION APPARATUS AND IMAGE RECONSTRUCTION METHOD

(71) Applicant: Hitachi, Ltd., Tokyo (JP)

(72) Inventors: Hisashi Takahashi, Tokyo (JP); Taiga Gotou, Tokyo (JP)

(73) Assignee: HITACHI, LTD., Tokyo (JP)

(*) Notice: Subject to any disclaimer, the term of this patent is extended or adjusted under 35 U.S.C. 154(b) by 107 days.

(21) Appl. No.: 16/666,931

(22) Filed: Oct. 29, 2019

(65) Prior Publication Data
US 2020/0151920 A1    May 14, 2020

(30) Foreign Application Priority Data
Nov. 12, 2018  (JP) .............................. JP2018-212005

(51) Int. Cl.
*G06T 5/00*    (2006.01)
*G06T 11/00*   (2006.01)
(Continued)

(52) U.S. Cl.
CPC ............ *G06T 11/008* (2013.01); *A61B 6/032* (2013.01); *A61B 6/5229* (2013.01);
(Continued)

(58) Field of Classification Search
CPC ......... G06T 3/40; G06T 3/4007; G06T 3/403; G06T 11/008; G06T 11/006; G06T 11/005; G06T 5/002; G06T 5/50; G06T 5/001; G06T 5/10; G06T 5/20; G06T 5/004; G06T 5/009; G06T 7/0012; G06T 2207/20224; G06T 2207/10081; G06T 2207/20182;
(Continued)

(56) References Cited

U.S. PATENT DOCUMENTS

2007/0140407 A1* 6/2007 Chen .................... A61B 6/5258
                                                    378/4
2008/0144900 A1* 6/2008 Li ...................... G01R 33/5611
                                                    382/130
(Continued)

FOREIGN PATENT DOCUMENTS

JP            5978429 B2    8/2016

*Primary Examiner* — Jose L Couso
(74) *Attorney, Agent, or Firm* — Foley & Lardner LLP (57) ABSTRACT

The present invention provides an image reconstruction apparatus and an image reconstruction method, both of which achieve reduction in a granular noise and a streak-like artifact both contained in a reconstruction image, and a clear structure boundary as well. The image reconstruction apparatus configured to generate a reconstruction image includes a noise reduction section that generates a streak reduction image as an image obtained by reducing a streak-like artifact in the reconstruction image, a noise reduction ratio acquisition section that acquires a first noise reduction ratio as a noise reduction ratio to be used for reducing a granular noise while retaining a structure boundary in the reconstruction image, and a second noise reduction ratio as a noise reduction ratio to be used for generating the streak reduction image, and an image addition section that adds an addition image to be generated based on the first noise reduction ratio and the second noise reduction ratio to the streak reduction image.

7 Claims, 9 Drawing Sheets

(51) Int. Cl.
  *G06T 5/50* (2006.01)
  *A61B 6/00* (2006.01)
  *A61B 6/03* (2006.01)
  *G06F 17/18* (2006.01)

(52) U.S. Cl.
  CPC ............ *A61B 6/5258* (2013.01); *G06F 17/18* (2013.01); *G06T 5/002* (2013.01); *G06T 5/50* (2013.01); *G06T 2207/10081* (2013.01); *G06T 2207/20224* (2013.01); *G06T 2210/41* (2013.01)

(58) Field of Classification Search
  CPC . G06T 2207/30004; G06T 2207/20028; G06T 2207/20056; G06T 2207/20192; G06T 2207/10016; G06T 2207/20012; G06T 2207/10116; G06T 2207/20212; G06T 2210/41; G06T 2211/424421; A61B 6/032; A61B 6/5229; A61B 6/5228; A61B 6/5205; A61B 6/5258; A61B 6/583; A61B 6/484; A61B 6/4085; A61B 6/482; A61B 6/4441; A61B 6/4021; A61B 6/405; G06F 17/18; G06K 9/40; H04N 5/21; H05G 1/30; Y10S 378/901
  See application file for complete search history.

(56) References Cited

U.S. PATENT DOCUMENTS

| | | | |
|---|---|---|---|
| 2009/0154787 A1* | 6/2009 | Bertram | G06T 11/005 382/132 |
| 2013/0094736 A1* | 4/2013 | Zamyatin | G06T 11/005 382/131 |
| 2014/0226887 A1 | 8/2014 | Takahashi | |
| 2017/0061653 A1* | 3/2017 | Hagiwara | A61B 6/5258 |
| 2017/0135659 A1* | 5/2017 | Wang | A61B 6/5258 |
| 2017/0172534 A1* | 6/2017 | Shieh | A61B 6/032 |
| 2018/0192985 A1* | 7/2018 | Maass | A61B 6/032 |
| 2019/0108904 A1* | 4/2019 | Zhou | G06K 9/66 |
| 2019/0365341 A1* | 12/2019 | Chan | G06T 7/0012 |
| 2020/0196974 A1* | 6/2020 | Schreiber | G06T 5/001 |

\* cited by examiner

|  | (a) ORIGINAL IMAGE | (b) BOUNDARY RETENTION IMAGE | (c) STREAK REDUCTION IMAGE | (d) OUTPUT IMAGE OF 2ND EMBODIMENT |
|---|---|---|---|---|
| NOISE REDUCTION RATIO | 0 | 0.16 | 0.50 | a=0.16<br>b=0.50 |
| MEASUREMENT SD VALUE | 59.8 | 50.7 | 31.4 | 49.7 |
| DEGREE OF REDUCTION IN STREAK-LIKE ARTIFACT | — | △ | ○ | ○ |
| BOUNDARY CLEARNESS | — | ○ | × | ○ |

IMAGE RECONSTRUCTION APPARATUS AND IMAGE RECONSTRUCTION METHOD

CLAIM OF PRIORITY

The present application claims priority from Japanese Patent Application JP 2018-212005 filed on Nov. 12, 2018, the content of which are hereby incorporated by references into this application.

TECHNICAL FIELD

The present invention relates to an image reconstruction apparatus and an image reconstruction method for generating a reconstruction image derived from an X-ray CT (Computed Tomography) apparatus, and specifically, relates to technology that achieves reduction in granular noise and streak-like artifact both contained in the reconstruction image, and a clear structure boundary as well.

BACKGROUND

The X-ray CT apparatus is configured to irradiate an X-ray to a periphery of an examinee, and to execute a back projection processing to the projection data acquired at a plurality of projection angles for generating a tomographic image so called the reconstruction image of the examinee. The generated reconstruction image is used for diagnosing the examinee.

The reconstruction image is formed by imaging a degree of the X-ray attenuation at the respective positions in the tomographic plane of the examinee, and contains noise owing to statistical fluctuation in the X-ray such as the granular noise and the streak-like artifact. The above-described noise may obscure the reconstruction image to hinder the diagnosis. Various noise reduction methods, thus, have been developed.

Japanese Patent No. 5978429 discloses that the projection data is grouped into subsets so that the noise reduction ratio is made uniform irrespective of the site in the body, and the weight to the penalty term contained in the evaluation function used for the method of successive approximation is calculated for each of the subsets. The weight calculated for each subset is used to implement the method of successive approximation. In Japanese Patent No. 5978429, the weight to the penalty term is correlated with each of the noise reduction ratios. It is therefore possible to generate the reconstruction image with desired noise reduction ratio irrespective of the site in the body.

In Japanese Patent No. 5978429, the granular noise and the streak-like artifact are equally treated. In some cases, the streak-like artifact exhibiting higher intensity than that of the granular noise cannot be sufficiently reduced. Prioritizing reduction in the streak-like artifact may obscure the structure boundary.

The present invention provides the image reconstruction apparatus and the image reconstruction method, both of which achieve reduction in the granular noise and the streak-like artifact both contained in the reconstruction image, and the clear structure boundary as well.

SUMMARY

The image reconstruction apparatus according to the present invention for generating the reconstruction image includes a noise reduction section that generates a streak reduction image as an image obtained by reducing a streak-like artifact in the reconstruction image, a noise reduction ratio acquisition section that acquires a first noise reduction ratio as a noise reduction ratio to be used for reducing a granular noise while retaining a structure boundary in the reconstruction image, and a second noise reduction ratio as a noise reduction ratio to be used for generating the streak reduction image, and an image addition section that adds an addition image to be generated based on the first noise reduction ratio and the second noise reduction ratio to the streak reduction image.

The image reconstruction method according to the present invention for generating the reconstruction image includes a noise reduction step of generating a streak reduction image as an image obtained by reducing a streak-like artifact in the reconstruction image, a noise reduction ratio acquisition step of acquiring a first noise reduction ratio as a noise reduction ratio to be used for reducing a granular noise while retaining a structure boundary in the reconstruction image, and a second noise reduction ratio as a noise reduction ratio to be used for generating the streak reduction image, and an image addition step of adding an addition image to be generated based on the first noise reduction ratio and the second noise reduction ratio to the streak reduction image.

The present invention provides the image reconstruction apparatus and the image reconstruction method, both of which achieve reduction in the granular noise and the streak-like artifact both contained in the reconstruction image, and the clear structure boundary as well.

DETAILED DESCRIPTION

Embodiments of the image reconstruction apparatus and the image reconstruction method according to the present invention will be described referring to the drawings. In the explanation and the drawings, the components with the same functions and structures will be designated with the same codes, and repetitive explanations thereof, thus will be omitted.

First Embodiment

Figure 1:
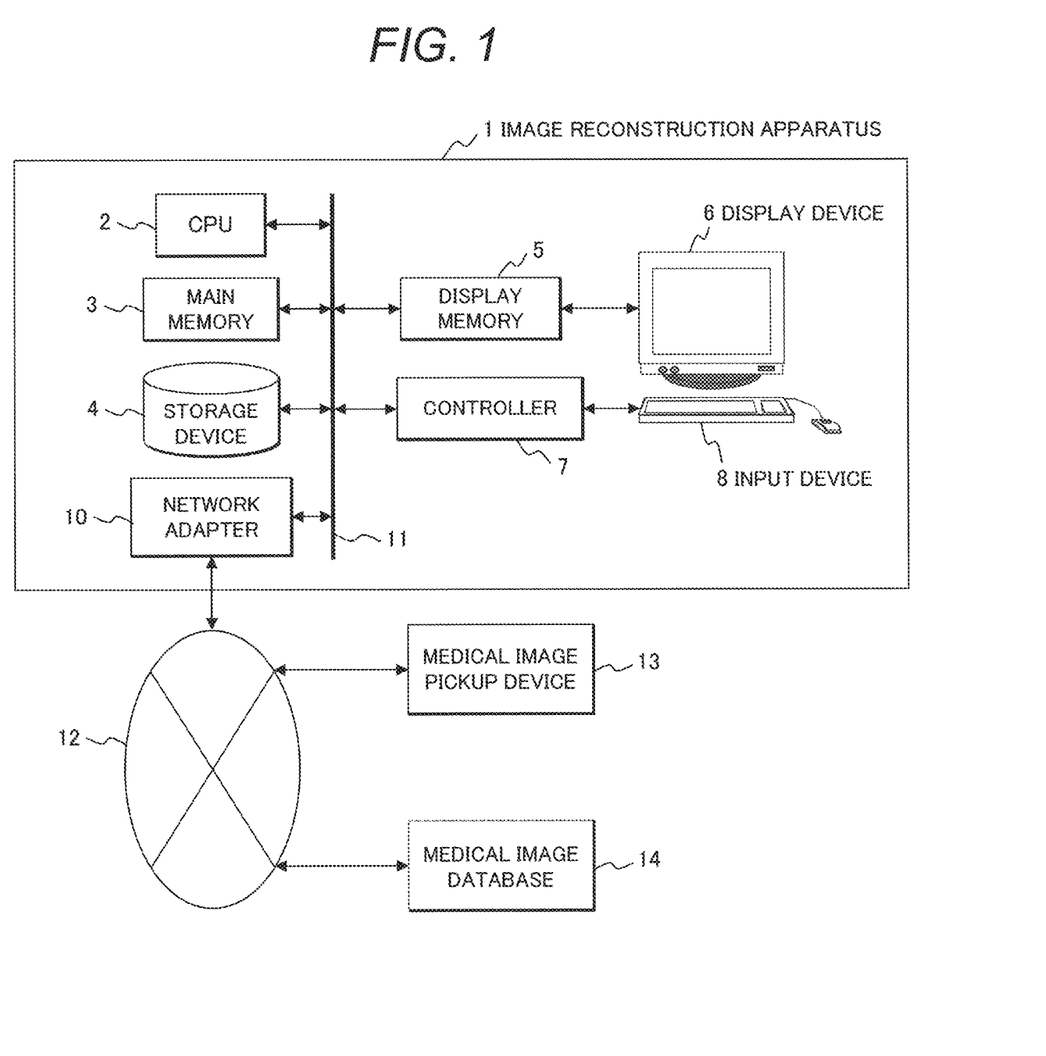
FIG. 1 shows an overall structure of an image reconstruction apparatus.

FIG. 1 illustrates a hardware structure of an image reconstruction apparatus 1. The image reconstruction apparatus 1 includes a CPU (Central Processing Unit) 2, a main memory 3, a storage device 4, a display memory 5, a display device 6, a controller 7, an input device 8, and a network adapter 10, all of which are connected via a system bus 11 so that signals are transmittable and receivable. The image reconstruction apparatus 1 is connected to a medical image pickup device 13 and a medical image database 14 via a network 12 so that signals are transmittable and receivable. The expression "signals are transmittable and receivable" represents the state that the signal may be bilaterally or unidirectionally transmittable and receivable electrically or optically between one and the other sides irrespective of either wiredly or wirelessly.

The CPU 2 controls operations of the respective components by loading the program to be stored in the storage device 4, and data necessary for executing the program in the main memory 3. The storage device 4 stores the program to be executed by the CPU 2, and the data necessary for executing the program, which may be in the form as HHD (Hard Disk Drive), and SSD (Solid state Drive). Various data is transmitted or received via the network 12 such as LAN (Local Area Network). The main memory 3 stores an on-going status of the program and an arithmetic process to be executed by the CPU 2.

The display memory 5 temporarily stores display data to be displayed on the display device 6 such as a liquid crystal display. The input device 8 such as a keyboard, a mouse, and a touch panel allows an operator to send an operation instruction to the image reconstruction apparatus 1. A pointing device, for example, a track pad, a trackball and the like may be used as the mouse. The controller 7 detects a state of the mouse to acquire a position of a mouse pointer on the display device 6, and outputs the acquired position information to the CPU 2. The network adapter 10 connects the image reconstruction apparatus 1 to the network 12 such as LAN, telephone line, and internet.

The medical image pickup device 13 acquires medical images such as tomographic images of the examinee. The medical image pickup device 13 may be an X-ray CT apparatus which will be described referring to FIG. 2. The medical image database 14 is a database system that stores the medical images acquired by the medical image pickup device 13.

Figure 2:
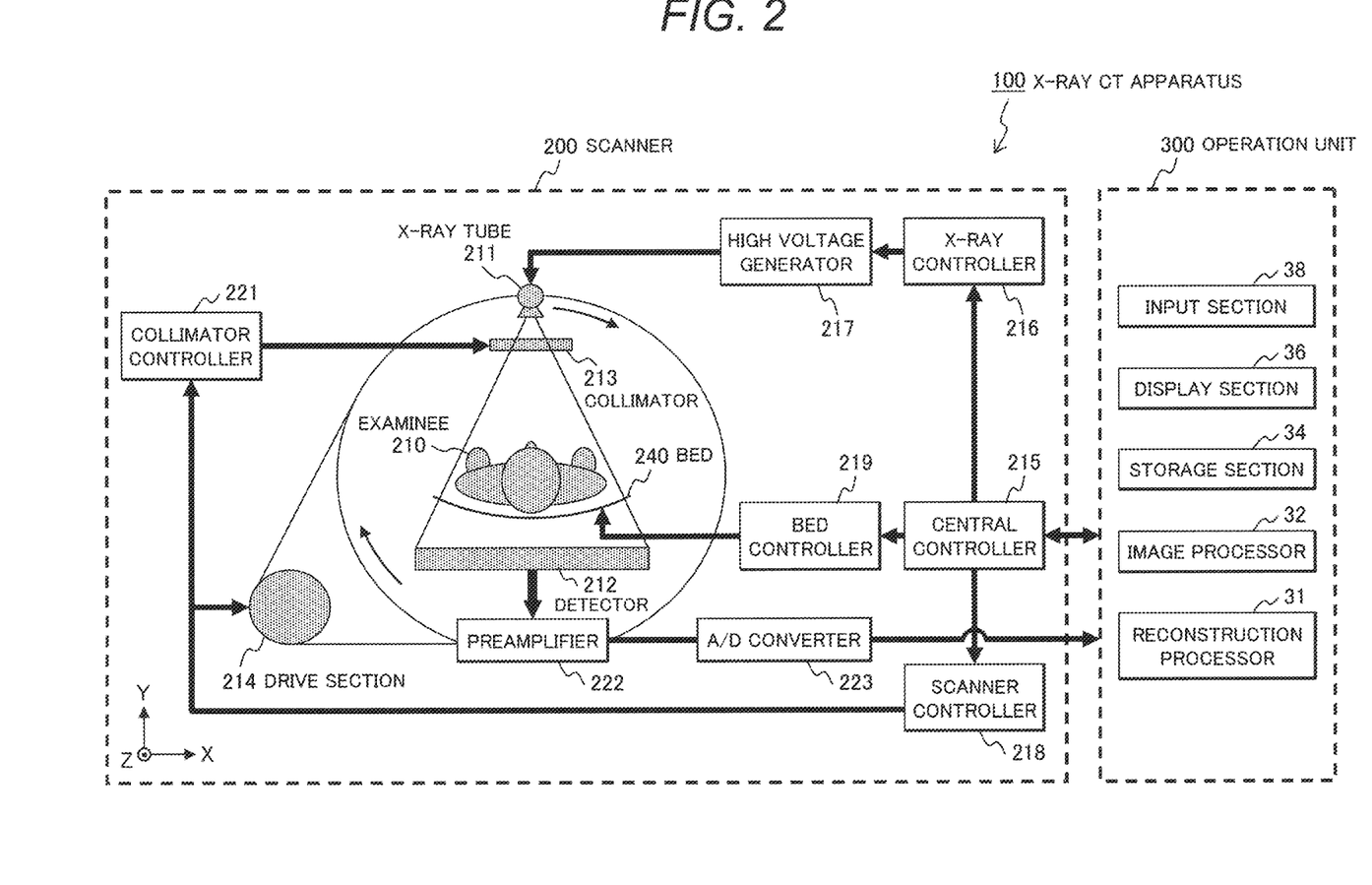
FIG. 2 shows an overall structure of an X-ray CT apparatus.

An overall structure of an X-ray CT apparatus 100 as an example of the medical image pickup device 13 will be described referring to FIG. 2. In FIG. 2, a horizontal direction is denoted as an X-axis, a vertical direction is denoted as a Y-axis, and a direction perpendicular to the drawing is denoted as a Z-axis. The X-ray CT apparatus 100 includes a scanner 200 and an operation unit 300. The scanner 200 includes an X-ray tube 211, a detector 212, a collimator 213, a drive section 214, a central controller 215, an X-ray controller 216, a high voltage generator 217, a scanner controller 218, a bed controller 219, a collimator controller 221, a preamplifier 222, an A/D converter 223, and a bed 240.

The X-ray tube 211 irradiates an X-ray to the examinee 210 on the bed 240. A high voltage generated by the high voltage generator 217 in accordance with a control signal transmitted from the X-ray controller 216 is applied to the X-ray tube 211 which in turn irradiates the X-ray to the examinee.

The collimator 213 restricts a range of the X-ray irradiated from the X-ray tube 211. The X-ray irradiation range is set in accordance with a control signal transmitted from the collimator controller 221.

The detector 212 detects the X-ray that has permeated through the examinee 210 so that a spatial distribution of the permeating X-ray is measured. The detector 212 disposed to confront the X-ray tube 211 includes many detecting elements two-dimensionally arrayed in a plane that faces the X-ray tube 211. The signal measured by the detector 212 is amplified by the preamplifier 222, and converted by the A/D converter 223 into a digital signal. Then various correction processing is executed to the digital signal to acquire the projection data.

The drive section 214 moves the X-ray tube 211 and the detector 212 around the examinee 210 in accordance with the control signal transmitted from the scanner controller 218. By executing the X-ray irradiation and detection while moving the X-ray tube 211 and the detector 212, the projection data at multiple projection angles is acquired. The data collection unit at each projection angle is referred to as a "view". In the two-dimensional array of the detection elements of the detector 212, a "channel" refers to the moving direction of the detector 212, and a "row" refers the direction orthogonal to the channel. The projection data is identified by the view, the channel, and the row.

The bed controller 219 controls operations of the bed 240. For example, the bed controller keeps the bed 240 stationary, or moves the bed 240 at constant speed in the Z-axis direction during irradiation and detection of the X-ray. The scanning to be performed while the bed 240 is kept stationary is called "axial scan", and the one to be performed while the bed 240 is moved is called "spiral scan".

The central controller 215 controls operations of the scanner 200 configured as described above in accordance with the instruction from the operation unit 300 to be described below. The operation unit 300 includes a reconstruction processor 31, an image processor 32, a storage section 34, a display section 36, and an input section 38.

The reconstruction processor 31 executes the back projection processing to the projection data acquired by the scanner 200 to generate the reconstruction image. The image processor 32 executes various types of image processing to make the reconstruction image suitable for diagnosis. The storage section 34 stores the projection data, the reconstruction images, and processed images. The display section 36 displays the reconstruction images and the processed images. The input section 38 is used by the operator for setting conditions of acquiring the projection data (tube voltage, tube current, scanning speed or the like), and reconstruction conditions (reconstruction filter, FOV size or the like) of the reconstruction image.

The operation unit 300 may be formed as the image reconstruction apparatus 1 as shown in FIG. 1. In this case, the image processor 32 corresponds to the CPU 2, the storage section 34 corresponds to the storage device 4, the display section 36 corresponds to the display device 6, and the input section 38 corresponds to the input device 8, respectively.

Figure 3A:
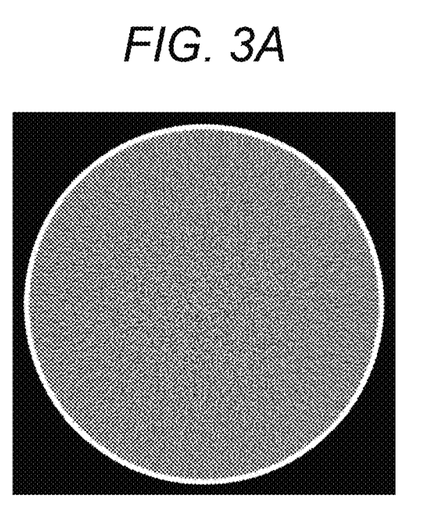
FIG. 3A and FIG. 3B illustrate exemplified noise as granular noise and streak-like artifact, respectively.
Figure 3B:
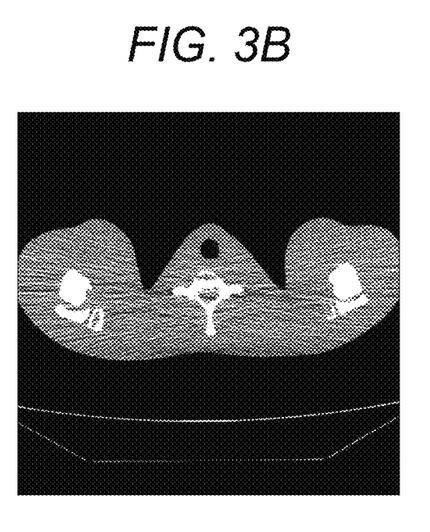

The granular noise and the streak-like artifact both contained in the reconstruction image will be described referring to FIG. 3A and FIG. 3B. The noise caused by the statistical fluctuation of the X-ray primarily depends on the cross-section shape of the examinee. If the cross-section shape is approximate to the perfect circle, the granular noise appears as shown in FIG. 3A. If the cross-section shape is approximate to an ellipse, for example, a shoulder part as shown in FIG. 3B, the linear noise, that is, the streak-like artifact appears in a longitudinal direction where the X-ray attenuation becomes large. The streak-like artifact that is hardly discriminated from the structure boundary on the reconstruction image is therefore required to be reduced together with the granular noise.

Japanese Patent No. 5978429 describes the method for reducing the streak-like artifact by smoothing the projection data, and further executing the back projection processing to the smoothed projection data. The method allows reduction in the streak-like artifact together with the granular noise. The noise reduction ratio may be controlled by adjusting the smoothing intensity. The noise reduction ratio NR is derived from the following formula using a standard deviation SDpre of the pixel value in a predetermined region of a pre-reduction image, and a standard deviation SDpst of the pixel value in the same region of a post-reduction image. Each of the standard deviations SDpre and SDpst is an SD (Standard Deviation) value that contains both the granular noise and the streak-like artifact.

$$NR=(SDpre-SDpst)/SDpre \qquad \text{(Formula 1)}$$

The higher the smoothing intensity becomes, the more the granular noise and the streak-like artifact are reduced. Conversely, however, the structure boundary becomes unclear. In the method of executing the back projection processing to the smoothed projection data, reduction in the noise contained in the reconstruction image, and the boundary clearness are in the tradeoff relation.

In this embodiment, aiming at achievement of both reduction in the granular noise and the streak-like artifact, and the clearness of structure boundary, an addition image that is produced in the process to be described below is added to a streak reduction image obtained by reducing the streak-like artifact in the reconstruction image. The addition image is generated based on the noise reduction ratio to be used for reducing the granular noise while retaining the structure boundary, and the noise reduction ratio to be used for generating the streak reduction image.

Figure 4:
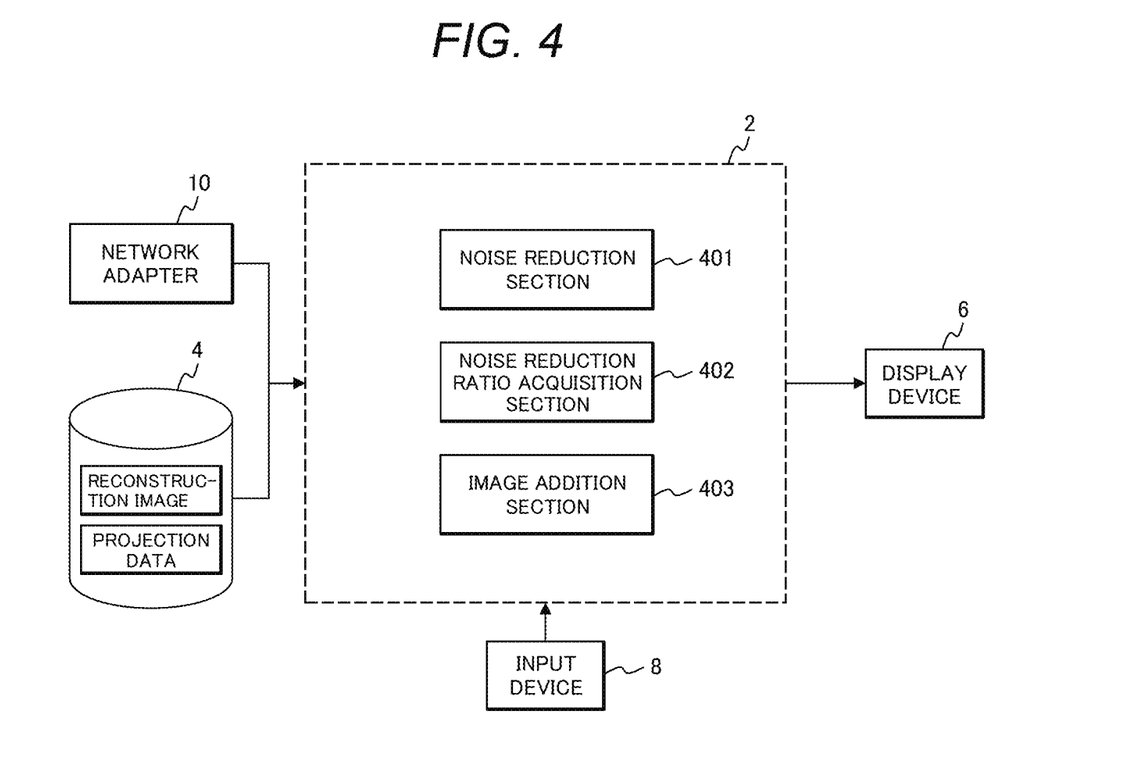
FIG. 4 is a function block diagram of a first embodiment.

An essential part of this embodiment will be described referring to FIG. 4. Those essential parts may be constituted by exclusive hardware, or software to be executed by the CPU 2. The explanation will be made on the assumption that the essential parts of this embodiment are constituted by the software.

This embodiment includes a noise reduction section 401, a noise reduction ratio acquisition section 402, and an image addition section 403. The storage device 4 stores the reconstruction images and projection data, which are generated in the X-ray CT apparatus 100. The respective components will be described hereinafter.

The noise reduction section 401 reduces the noise in the reconstruction image. The noise in the reconstruction image may be reduced by smoothing the projection data, and further executing the back projection processing to the smoothed projection data, or by smoothing the reconstruction image. The projection data and the reconstruction images are read from the storage device 4, or externally transmitted via the network adapter 10. The noise reduction section 401 may be configured to reduce the noise in the reconstruction image based on the noise reduction ratio. The noise reduction section 401 reduces the noise in the reconstruction image to generate at least the streak reduction image as the image obtained by reducing the streak-like artifact.

The noise reduction ratio acquisition section 402 acquires the noise reduction ratio to be used for reducing the noise in the reconstruction image. The noise reduction ratio may be set by the operator through the input device 8, or calculated based on each size of the granular noise and the streak-like artifact in the reconstruction image. In this embodiment, the noise reduction ratio to be used for reducing the granular noise while retaining the structure boundary in the reconstruction image is denoted as a first noise reduction ratio, and the noise reduction ratio to be used for generating the streak reduction image is denoted as a second noise reduction ratio. The image obtained by reducing the granular noise while retaining the structure boundary in the reconstruction image is denoted as a boundary retention image.

The image addition section 403 adds the addition image generated based on the first noise reduction ratio and the second noise reduction ratio to the streak reduction image. It is possible to generate an image having both the glandular noise and the streak-like artifact reduced, and the clear structure boundary by adding the addition image to the streak reduction image. The image generated by the image addition section 403 is displayed on the display device 6.

Figure 5:
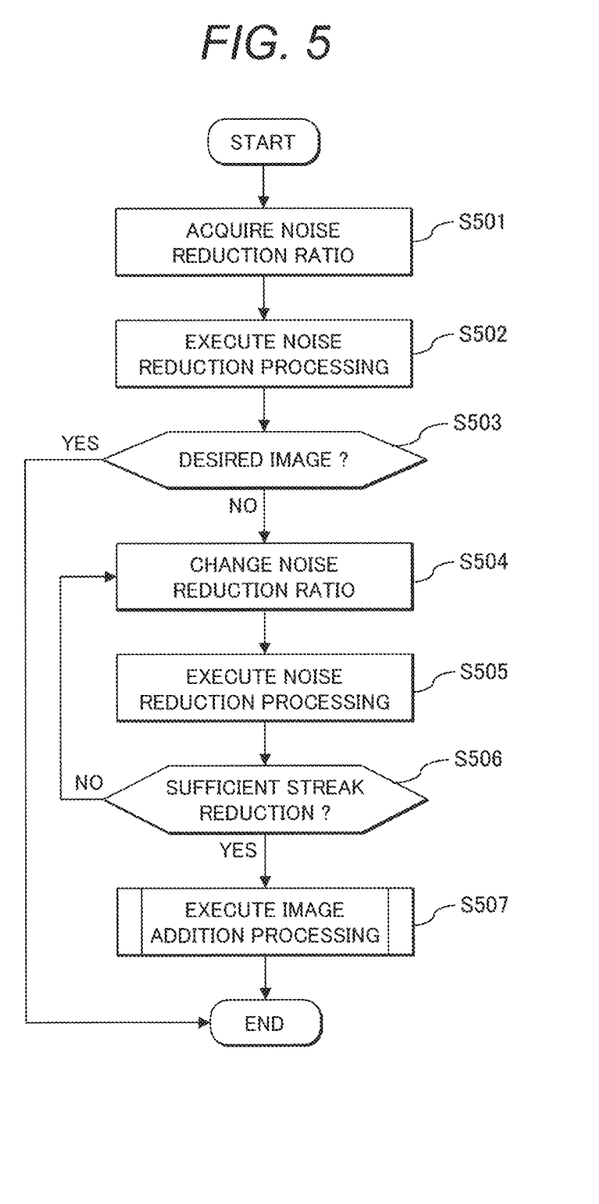
FIG. 5 is a flowchart showing a process flow according to the first embodiment.

An example of the process flow to be executed in the embodiment will be described referring to FIG. 5.

(S501)

Figure 6:
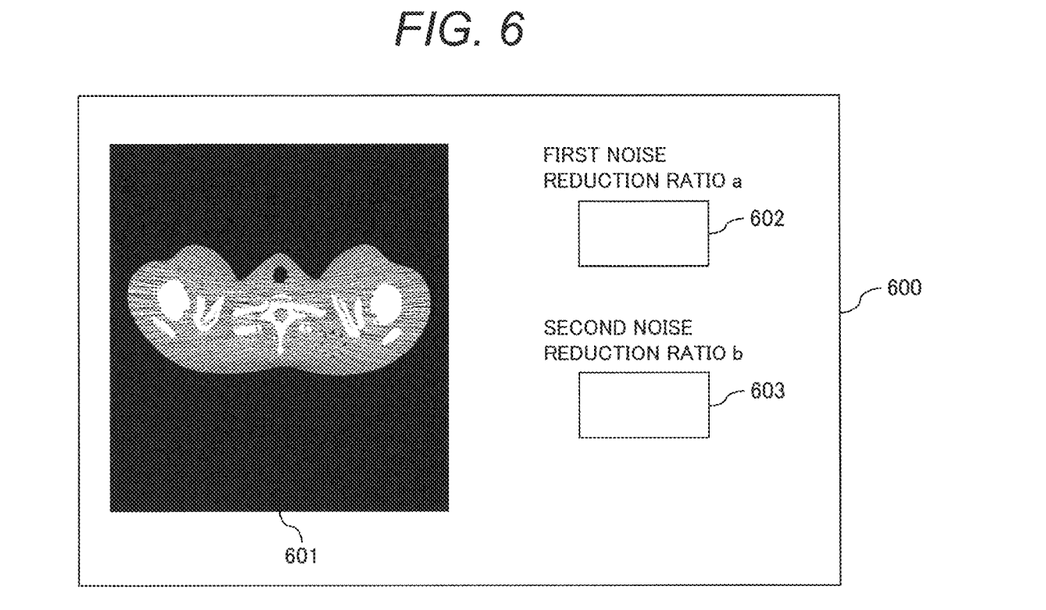
FIG. 6 shows an example of an input screen according to the first embodiment.

The noise reduction ratio acquisition section 402 acquires the noise reduction ratio. For example, the noise reduction ratio input by the operator is acquired via an input screen 600 as shown in FIG. 6. The input screen 600 includes an image display section 601, a first noise reduction ratio input section 602, and a second noise reduction ratio input section 603. The operator inputs the noise reduction ratio either in the first noise reduction ratio input section 602 or the second noise reduction ratio input section 603. The image display section 601 displays the reconstruction image and the like.

The noise reduction ratio acquisition section 402 may be configured to acquire the noise reduction ratio derived from calculation based on a preliminarily obtained size of the noise in the reconstruction image. For example, the noise reduction ratio NR may be derived from calculating the formula 1 using SDpre as the size of noise in the reconstruction image, and a target value of SDpst as the size of noise in the image having the noise reduced.

(S502)

The noise reduction section 401 reduces the noise in the reconstruction image based on the noise reduction ratio acquired in S501. For example, after smoothing the projection data based on the noise reduction ratio, the back projection processing is executed to the smoothed projection data to generate the reconstruction image having the noise reduced.

(S503)

It is determined whether or not the image generated in S501 is a desired image. If it is determined that the desired image is obtained, the process ends. If it is determined that the desired image is not obtained because of the image, for example, having the clear structure boundary, but insufficiency of reduction in the streak-like artifact, the process proceeds to S504. The operator is allowed to determine whether or not the desired image has been obtained by visually observing the image displayed on the image display section 601 of the input screen 600. Alternatively, the image reconstruction apparatus 1 is allowed to make the determination based on a predetermined index value.

(S504)

The noise reduction ratio acquisition section 402 acquires the changed noise reduction ratio. For example, the noise reduction ratio that has been input by the operator in the second noise reduction ratio input section 603 of the input screen 600 is acquired as the changed ratio. In this case, the noise reduction ratio before change is stored as the first noise reduction ratio a in the main memory 3 and the storage device 4. The noise reduction ratio after change is stored as the second noise reduction ratio b. If it is determined that the image has the clear structure boundary, but insufficiency of reduction in the streak-like artifact, the process proceeds to this step where the noise reduction ratio is changed to the larger value (a<b) for further noise reduction.

If the noise reduction ratio is changed by the image reconstruction apparatus 1 rather than by the operator, the predetermined value set as the noise reduction ratio before change, for example, 0.1 is added. The value to be added is not limited to 0.1 but may be an arbitrary value so long as the noise reduction ratio does not exceed the value 1. Alternatively, noise reduction ratios experimentally calculated using a human body type phantom are preliminarily stored in the storage device 4 in correlation with the image pickup conditions and reconstruction conditions to allow the use of the noise reduction ratio to be read in accordance with the set image pickup conditions and reconstruction conditions.

The first and the second noise reduction ratios may be calculated based on the reconstruction image, the boundary retention image, and the streak reduction image. Using the SDpre as a standard deviation of pixel values in a predetermined region of the reconstruction image, and the SDpst as a standard deviation of pixel values in the same region of the boundary retention image, the formula 1 is calculated to obtain the NR as the first noise reduction ratio. Likewise, using the SDpre as the standard deviation of the reconstruction image, and the SDpst as the standard deviation of the streak reduction image, the formula 1 is calculated to obtain the NR as the second noise reduction ratio.

(S505)

The noise reduction section 401 reduces the noise of the reconstruction image based on the noise reduction ratio acquired in S504.

(S506)

It is determined whether or not the streak-like artifact in the image generated in S505 has been sufficiently reduced. If it is determined that the streak-like artifact has been sufficiently reduced, that is, the streak reduction image is generated, the process proceeds to S507. If it is determined that the reduction in the streak-like artifact is insufficient, the process returns to S504 where the noise reduction ratio is further changed. The determination on sufficient reduction in the streak-like artifact may be made through visual observation performed by the operator, or by the image reconstruction apparatus 1 based on the predetermined index value. The image obtained by sufficiently reducing the streak-like artifact is stored in the storage device 4 as the streak reduction image.

(S507)

Figure 7:
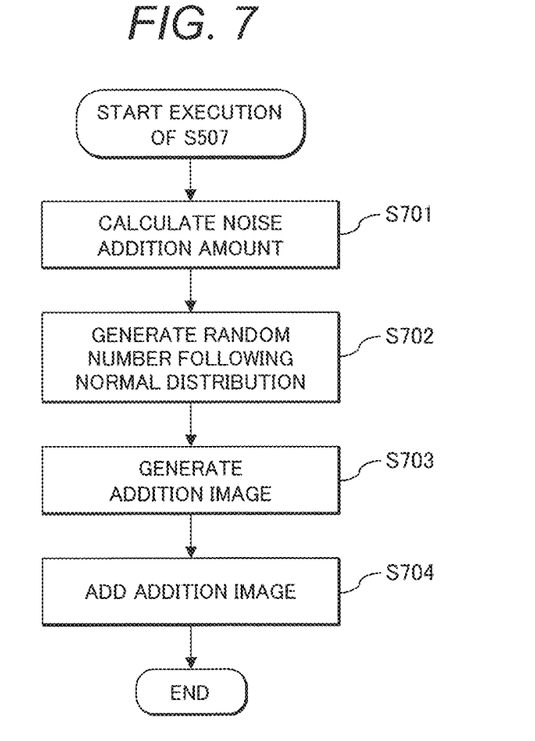
FIG. 7 is a flowchart representing an image addition process according to the first embodiment.

The image addition section 403 adds the addition image generated based on the first and the second noise reduction ratios to the streak reduction image generated in S505. Mostly, the streak reduction image has the streak-like artifact sufficiently reduced, but has the unclear structure boundary. In this step, the addition image is added to the streak reduction image with unclear boundary to clarify the boundary without increasing the streak-like artifact. The addition image does not contain the streak-like artifact, but contains the granular noise as well as the information relating to the structure boundary. In other words, the noise amount of the image obtained by adding the addition image to the streak reduction image is made equivalent to that of the image with clear boundary. The resultant image has the clear boundary without increasing the streak-like artifact although the granular noise is increased compared with the streak reduction image. An example of the process flow in S507 is shown in FIG. 7, and each step will be described.

(S701)

The image addition section 403 calculates the noise addition amount, that is, the amount of noise of the addition image. Before calculating the noise addition amount, the noise amount of the streak reduction image is calculated in the following manner. The projection data of the streak reduction image, that is, data smoothed based on the second noise reduction ratio is divided into two projection data pieces of even-numbered views and odd-numbered views to generate a difference image between the reconstruction images generated from the respective projection data pieces. The generated difference image becomes a noise map that reflects the noise amount of each pixel of the streak reduction image. It is therefore possible to calculate the noise amount, that is, the SD value for each pixel. It is assumed that the index of the pixel of the streak reduction image is defined as j(j=1, . . . J), and the SD value of the j-th pixel derived from the noise map is set to $u_j$(j=1, . . . J) for explanation to be made as follows.

Figure 8:
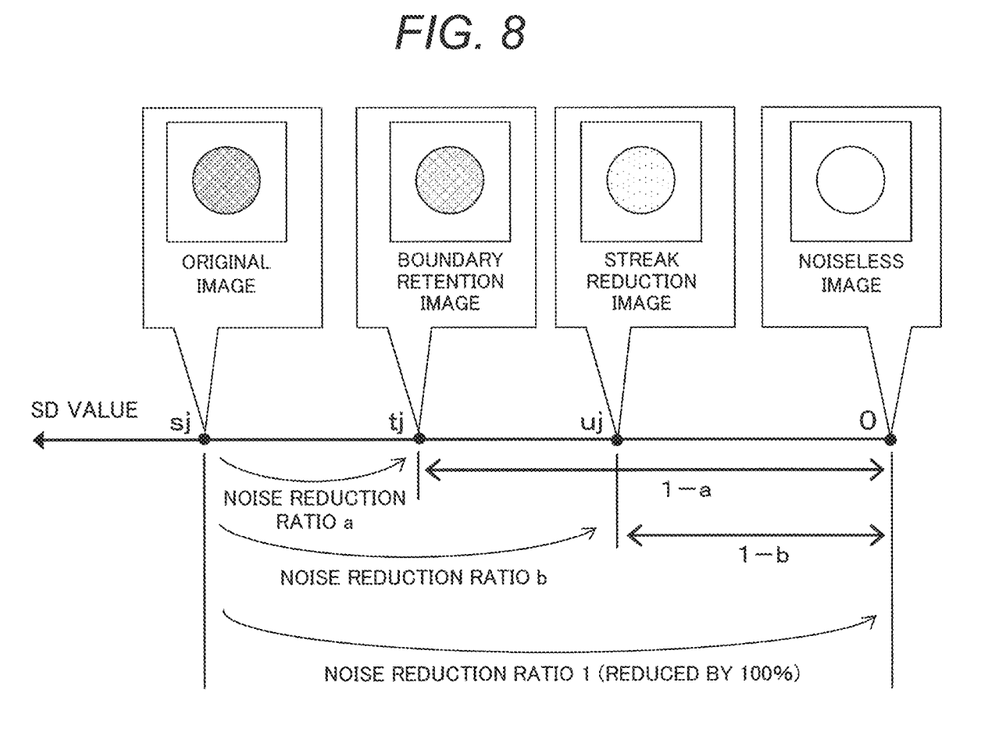
FIG. 8 is a supplementary explanatory view of the first embodiment.

Based on the noise amount $u_j$ of the streak reduction image, the noise addition amount $\sigma_j$ is calculated. Referring to FIG. 8, calculation of the noise addition amount $\sigma_j$ will be described. FIG. 8 is a conceptual view showing a relation between the SD value and the noise reduction ratio. An original image as an unsmoothed reconstruction image, a boundary retention image, a streak reduction image, and a noiseless image as an image having noise completely removed are arranged along a horizontal axis indicating the SD value. The SD values of the j-th pixel of the respective images are denoted as "$s_j$", "$t_j$", "$u_j$", and "0". The boundary retention image is generated based on the first noise reduction ratio a, and the streak reduction image is generated based on the second noise reduction ratio b. The original image and the noiseless image are not used herein, but shown only for the purpose of explanation.

In accordance with the formula 1, the correlations as shown in FIG. 8 may be expressed as follows: $a=(s_j-t_j)/s_j$, and $b=(s_j-u_j)/s_j$. Those formulae provide the formula of $t_j=u_j \times (1-a)/(1-b)$. The noise addition amount $\sigma_j$ that changes the SD value from $u_j$ to $t_j$ may be derived from $\sigma_j=t_j-u_j$, leading to the formula of $\sigma_j=u_j \times (b-a)/(1-b)$. In other words, the noise addition amount $\sigma_j$ is calculated based on the first noise reduction ratio a and the second noise reduction ratio b.

(S702)

The image addition section 403 generates a random number following a normal distribution to bring the average value to 0, and the standard deviation to 1. For example, Box-Muller method is used to generate the random number from the one following the uniform distribution. The random number may be generated using various known methods.

(S703)

The image addition section 403 generates the addition image by multiplying the noise addition amount $\sigma_j$ of the j-th pixel calculated in S701 by the random number generated in S702.

(S704)

The image addition section 403 adds the addition image generated in S703 to the streak reduction image.

Execution of the process flow as described above generates the image having both the granular noise and the streak-like artifact reduced, and the clear structure boundary. This allows the operator to obtain the medical image suitable for diagnosis.

Second Embodiment

In the first embodiment, the addition image is generated using the random number following the normal distribution. This embodiment describes generation of the addition image using the difference image between the streak reduction image and the smoothed image obtained by smoothing the streak reduction image. This embodiment is different from the first embodiment in the image addition process to be executed in S507 as shown in FIG. 5. The explanation of the process other than the image addition process will be omitted.

Figure 9:
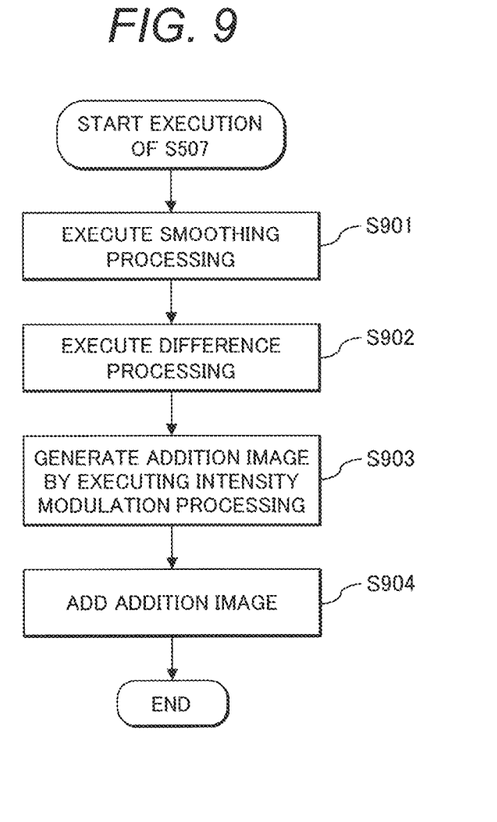
FIG. 9 is a flowchart representing an image addition process according to a second embodiment.
Figure 10:
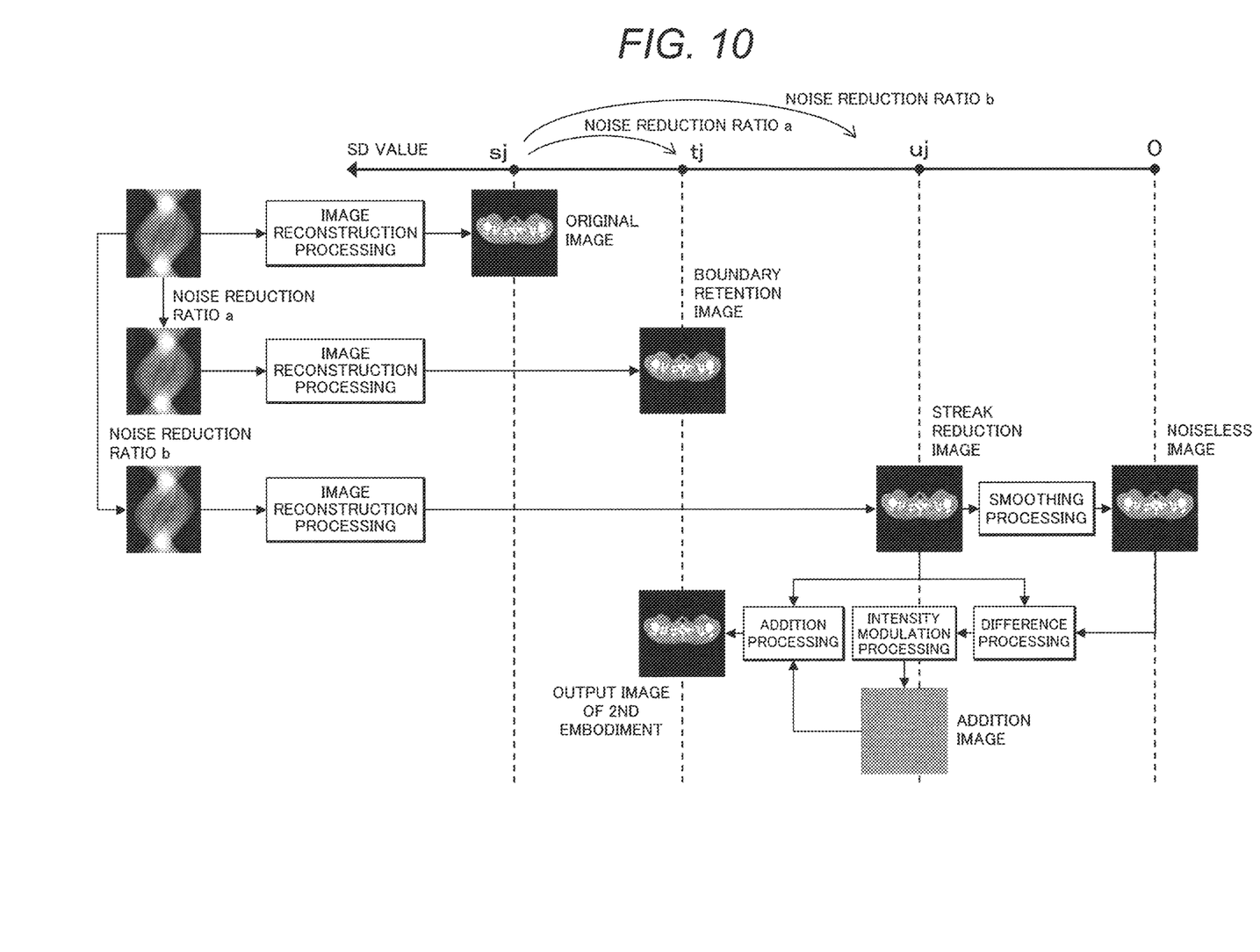
FIG. 10 is a supplementary explanatory view of the second embodiment.

The image addition process according to the embodiment will be described referring to FIG. 9, and FIG. 10 as needed for conceptually showing the relation between the SD value and the noise reduction ratio.

(S901)

The image addition section 403 executes the smoothing process to the streak reduction image. In other words, the noiseless image is generated by reducing the noise component from the streak reduction image. Referring to FIG. 10, the smoothing process is executed to the streak reduction image with the SD value u to generate the noiseless image with the SD value of substantially zero. It is possible to use the known method such as the TV (Total Variation) filter, NLM (Non-Local Means) filter and the like for executing the smoothing process in this step. The use of those filters substantially removes the fine noise component while retaining the local signal component in the image. This lows extraction of the information relating to the structure boundary.

(S902)

The image addition section 403 generates the difference image between the streak reduction image and the noiseless image generated in S901. The difference process is executed to obtain the difference between the streak reduction image with the SD value $u_j$ and the noiseless image with the SD value of substantially zero as shown in FIG. 10. The difference image generated in this step contains the information relating to the noise component other than the streak-like artifact and the structure boundary. Since the SD value of the noiseless image is substantially zero, the SD value of the difference image is substantially the same as the SD value $u_j$ of the streak reduction image.

(S903)

The image addition section 403 generates the addition image by executing intensity modulation to the difference image generated in S902. Referring to FIG. 10, the intensity modulation processing is executed to the difference image derived from the process to obtain the difference between the streak reduction image and the noiseless image so that the addition image is generated. The intensity modulation to the difference image is executed so that the SD value of the image generated by adding the addition image to the streak reduction image becomes substantially the same as the SD value t of the boundary retention image. In other words, the intensity modulation is executed to the respective pixels of the difference image using the magnification (b−a)/(1−b) to generate the addition image. Since the difference image has the streak-like artifact sufficiently reduced, the addition image to be generated also has the streak-like artifact sufficiently reduced.

If accuracy of the smoothing processing in S901 is low, the SD value of the noiseless image no longer becomes substantially zero. Accordingly, the difference in the SD values between the difference image and the streak reduction image becomes large. In step S903, the SD value $v_j$ may be calculated using pixel values of a plurality of pixels located adjacent to the j-th pixel of the difference image. Then the calculated value may be calibrated to $u_j$ to execute the intensity modulation to the difference image using the magnification of $u_j(b-a)/v_j(1-b)$. Execution of the intensity modulation allows reduction in the difference of the SD values between the difference image and the streak reduction image. If generation of the noiseless image needs a long period, the image with the substantially non-zero SD value that can be generated for a short period may be used instead of the noiseless image to allow execution of the intensity modulation to the difference image with the magnification of $u_j(b-a)/v_j(1-b)$.

(S904)

The image addition section 403 adds the addition image generated in S903 to the streak reduction image. Referring to FIG. 10, the addition process is executed by adding the addition image to the streak reduction image with the SD value $u_j$ to generate the output image of the embodiment. The SD value of the output image becomes equivalent to the SD value $t_j$ of the boundary retention image. Although the addition image having the streak-like artifact reduced is added to the streak reduction image having the streak-like artifact reduced, the streak-like artifact is not increased.

Execution of the above-described process flow generates the image having both the granular noise and the streak-like artifact reduced, and the clear structure boundary so that the operator obtains the medical image suitable for diagnosis. It is possible to generate the output image by adding the image derived from intensity modulating the respective pixels of the difference image generated in S902 by (1−a)/(1−b) times to the noiseless image generated in S901.

Figure 11A:
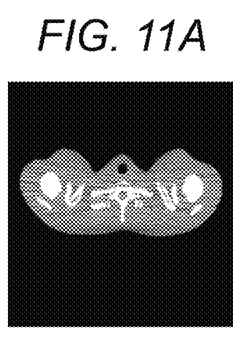
FIG. 11A to FIG. 11E illustrate an example of an advantageous effect of the second embodiment.
Figure 11B:
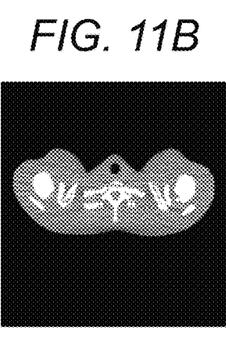
Figure 11C:
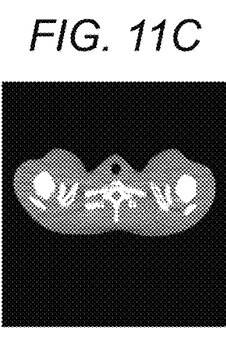
Figure 11D:
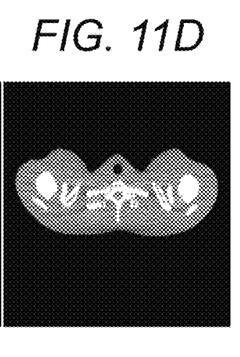
Figure 11E:
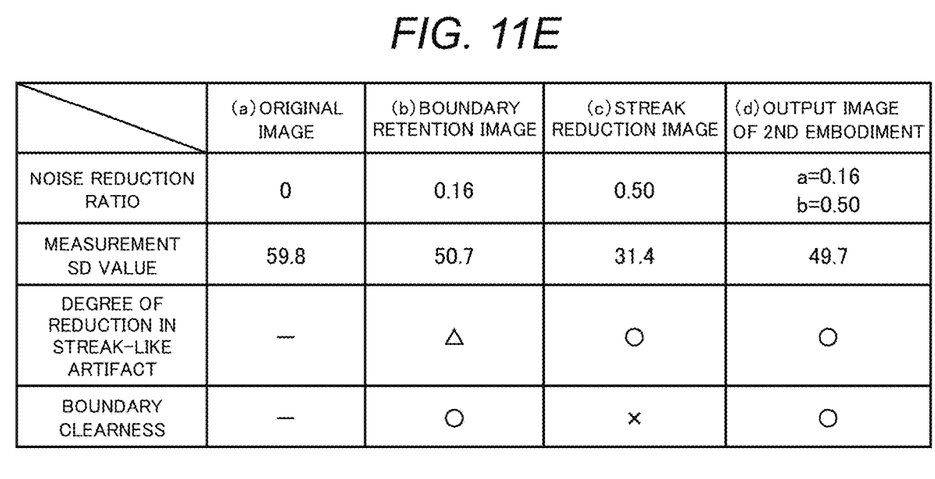

Images derived from the embodiment will be described referring to FIG. 11A to FIG. 11E. FIG. 11A shows an original image formed by scanning the shoulder part of the phantom. FIG. 11B shows an image generated by smoothing the projection data of the original image while having the noise reduction ratio set to 0.16. FIG. 11C shows an image generated by setting the noise reduction ratio to 0.50. FIG. 11D shows an output image of the embodiment. FIG. 11B corresponds to the boundary retention image, and FIG. 11C corresponds to the streak reduction image. The output image of the embodiment is generated by setting the first noise reduction ratio to 0.16, and the second reduction ratio to 0.50. FIG. 11E is a table for comparing the images of FIG. 11A to FIG. 11D with respect to the noise reduction ratio, the measurement SD value, the degree of reduction in the streak-like artifact, and the boundary clearness. The measurement SD value is obtained as a result of measuring the SD value of the pixel value in the region enclosed in dotted line of the respective images. The degree of reduction in the streak-like artifact, and the boundary clearness are obtained as a result of comparison with the original image, and evaluation through visual observation.

The measurement SD values of the boundary retention image and the streak reduction image are 50.7 and 31.4, respectively in comparison with the SD value 59.8 of the original image. Those values indicate that the noise has been reduced by the amount corresponding to the set noise reduction ratio. Compared with the original image, the streak-like artifact of the boundary retention image has been reduced insufficiently, and the streak-like artifact of the streak reduction image has been reduced sufficiently. The boundary clearness of the boundary retention image is equivalent to that of the original image. Meanwhile, the streak reduction image exhibits unclear as indicated by a white bone region that is partially expanded.

As for the output image of the second embodiment, the measurement SD value is 49.7 which is equivalent to that of the boundary retention image. The degree of reduction in the stream-like artifact is equivalent to that of the streak reduction image, and the boundary clearness is equivalent to that of the boundary retention image. The embodiment achieves generation of the image having both the granular noise and the streak-like artifact reduced, and the clear structure boundary.

The image reconstruction apparatus and the image reconstruction method are not limited to the above-described embodiments, but may be implemented by modifying the components so long as they do not deviate from the scope of the invention. The plurality of components as described in the embodiments may be arbitrarily combined, or some components may be eliminated from all the components.

LIST OF REFERENCE SIGNS

1: image reconstruction apparatus, 2: CPU, 3: main memory, 4: storage device, 5: display memory, 6: display device, controller, 8: input device, 10: network adapter, 11: system bus, 12: network, 13: medical image pickup device, 14: medical image database, 100: X-ray CT apparatus, 200: scanner, 210: examinee, 211: X-ray tube, 212: detector, 213: collimator, 214: drive section, 215: central controller, 216: X-ray controller, 217: high voltage generator, 218: scanner controller, 219: bed controller, 221: collimator controller, 222: preamplifier, 223: A/D converter, 240: bed, 300: operation unit, 31: reconstruction processor, 32: image processor, 34: storage section, 36: display section, 38: input section, 401: noise reduction section, 402: noise reduction ratio acquisition section, 403: image addition section, 600: input screen, 601: image display section, 602: first noise reduction ratio input section, 603: second noise reduction ratio input section

What is claimed is:

1. An image reconstruction apparatus for generating a reconstruction image, comprising:
   a processor programmed to:
   generate a streak reduction image as an image obtained by reducing a streak-like artifact in the reconstruction image;
   acquire a first noise reduction ratio as a noise reduction ratio to be used for reducing a granular noise while retaining a structure boundary in the reconstruction image, and a second noise reduction ratio as a noise reduction ratio to be used for generating the streak reduction image;
   add an addition image to be generated based on the first noise reduction ratio and the second noise reduction ratio to the streak reduction image; and
   generate the addition image by executing intensity modulation to a difference image between the streak reduction image and a smoothed image obtained by smoothing the streak reduction image by a magnification to be calculated based on the first noise reduction ratio and the second noise reduction ratio.

2. The image reconstruction apparatus according to claim 1, wherein the processor is programmed to generate the addition image by multiplying a noise addition amount calculated based on the first noise reduction ratio and the second noise reduction ratio by a random number following a normal distribution.

3. The image reconstruction apparatus according to claim 1, wherein if a noise amount of the smoothed image is not substantially zero, the difference image is intensity-modified by a magnification calibrated based on an SD value to be calculated using pixel values of a plurality of pixels located adjacent to a target pixel of the difference image.

4. The image reconstruction apparatus according to claim 1, wherein the processor is programmed to acquire the first noise reduction ratio and the second noise reduction ratio via a screen on which the noise reduction ratio is input.

5. An image reconstruction apparatus for generating a reconstruction image, comprising:
   a processor programmed to:
   generate a streak reduction image as an image obtained by reducing a streak-like artifact in the reconstruction image;
   acquire a first noise reduction ratio as a noise reduction ratio to be used for reducing a granular noise while retaining a structure boundary in the reconstruction image, and a second noise reduction ratio as a noise reduction ratio to be used for generating the streak reduction image;
   add an addition image to be generated based on the first noise reduction ratio and the second noise reduction ratio to the streak reduction image;
   generate a boundary retention image as an image obtained by reducing the granular noise while retaining the structure boundary in the reconstruction image; and
   calculate the first noise reduction ratio from noise amounts of both the reconstruction image and the boundary retention image, and the second noise reduction ratio from noise amounts of both the reconstruction image and the streak reduction image.

6. The image reconstruction apparatus according to claim 1, wherein the first noise reduction ratio is smaller than the second noise reduction ratio.

7. An image reconstruction method for generating a reconstruction image comprising:
   generating a streak reduction image as an image obtained by reducing a streak-like artifact in the reconstruction image;
   acquiring a first noise reduction ratio as a noise reduction ratio to be used for reducing a granular noise while retaining a structure boundary in the reconstruction image, and a second noise reduction ratio as a noise reduction ratio to be used for generating the streak reduction image;
   adding an addition image to be generated based on the first noise reduction ratio and the second noise reduction ratio to the streak reduction image; and
   generate the addition image by executing intensity modulation to a difference image between the streak reduction image and a smoothed image obtained by smoothing the streak reduction image by a magnification to be calculated based on the first noise reduction ratio and the second noise reduction ratio.

* * * * *